US005965737A

United States Patent [19]

Prasad et al.

[11] Patent Number: 5,965,737

[45] Date of Patent: Oct. 12, 1999

[54] APPROACH TO THE CONVERSION OF 2-(METHYLTHIO)-5-(TRIFLUOROMETHYL)-1,3,4-THIADIAZOLE (TDA) TO 2-(METHYLSULFONYL)-5-(TRIFLUOROMETHYL)-1,3,4-THIADIAZOLE (TDA SULFONE)

[75] Inventors: Vidyanatha A. Prasad, Leawood, Kans.; Joe J. Hanson, Blue Springs, Mo.; Klaus Jelich, Overland Park, Kans.

[73] Assignee: Bayer Corporation, Pittsburgh, Pa.

[21] Appl. No.: 09/251,571

[22] Filed: Feb. 17, 1999

[51] Int. Cl.$^{6}$ .............................................. C07D 285/125

[52] U.S. Cl. ............................................................ 548/136

[58] Field of Search ............................................ 548/136

[56] References Cited

U.S. PATENT DOCUMENTS 3,562,284 2/1971 Newman et al. ...................... 260/302

5,856,449 1/1999 Prasad .................................... 548/136

OTHER PUBLICATIONS

Durst, T., in Comprehensive Organic Chemistry: Chapter 11.6, Barton and Ollis, Eds., Pergammon Press, Oxford, (month unavailable) 1979.

*Primary Examiner*—Robert Gerstl
*Attorney, Agent, or Firm*—Joseph C. Gil; Carol Marmo

[57] ABSTRACT

The present invention provides a process for making thiadiazole sulfones. In particular, the present process is used to make 2-(methyl-sulfonyl)-5-(trifluoromethyl)-1,3,4-thiadiazole using catalytic oxidation in the presence of a suitable oxidizing agent. A preferred oxidizing agent is hydrogen peroxide. The catalyst system used for the oxidation reaction is a mixture of boric acid and glacial acetic acid. The molar ratio of glacial acetic acid to 2-(methylthio)-5-(trifluoromethyl)-1,3,4-thiadiazole is from about 0.1:1 to about 0.5:1.

14 Claims, No Drawings

APPROACH TO THE CONVERSION OF 2-(METHYLTHIO)-5-(TRIFLUOROMETHYL)-1,3,4-THIADIAZOLE (TDA) TO 2-(METHYLSULFONYL)-5-(TRIFLUOROMETHYL)-1,3,4-THIADIAZOLE (TDA SULFONE)

TECHNICAL FIELD OF THE INVENTION

The field of the present invention is the synthesis of thiadiazole sulfones. More particularly, the present invention pertains to an improved process for converting 2-(methylthio)-5-(trifluoromethyl)-1,3,4-thiadiazole (TDA) to 2-(methylsulfonyl)-5-(trifluoromethyl)-1,3,4-thiadiazole (TDA sulfone) via a catalytic oxidation.

BACKGROUND OF THE INVENTION

Sulfones have the general structure $RR'SO_2$. Sulfones can be produced from a variety of precursors. For example, sulfones can be prepared by (a) oxidizing sulphides, (b) rearranging sulphinate esters, (c) adding sulfonyl halides to alkenes and acetylenes, (d) adding sulphinic acids to polarized bonds, and (e) adding $SO_2$ to polyenes (See, e.g., Durst, T., in *Comprehensive Organic Chemistry:* Chapter 11.6, Barton and Ollis, Eds., Pergammon Press, Oxford, 1979).

A particular class of sulfones, 2-(alkylsulfonyl)-5-(trifluoro-methyl)-1,3,4-thiadiazoles, are intermediates used in the production of herbicides. A particular sulfone within this class, 2-(methylsulfonyl)-5-(trifluoro-methyl)-1,3,4-thiadiazole, has been reported to possess antifungal activity (See, U.S. Pat. No. 3,562,284). According to U.S. Pat. No. 3,562,284, 2-(substituted sulfonyl)-5-(trifluoromethyl)-1,3,4-thiadiazoles can be made by oxidizing a corresponding 2-(substituted thio)-5-(trifluoromethyl)-1,3,4-thiadiazole in the presence of an oxidizing agent such as potassium permanganate, hydrogen peroxide or peroxytrifluoro-acetic acid. Oxidation takes place in an acidic, aqueous medium that includes acetic acid and methylene chloride as a solvent. Methylene chloride is an undesirable solvent from the standpoint of industrial hygiene and handling. Handling is difficult due to its low boiling point (high vapor pressure). In addition, it contaminates aqueous streams. The sulfone product is isolated using crystallization. The reported yield of the sulfone, based on the starting sulfide, is about 65%.

In this known process, the use of acetic acid in the presence of water introduces excess water into the reaction and requires purification of the sulfone using expensive crystallization procedures with resultant low yields. Thus, there continues to be a need in the art for a practical, inexpensive process for preparing thiadiazole sulfones in high yield.

BRIEF SUMMARY OF INVENTION

The present invention provides a process for making 2-(methylsulfonyl)-5-(trifluoromethyl)-1,3,4-thiadiazole comprising oxidizing 2-(methylthio)-5-(trifluoromethyl)-1,3,4-thiadiazole in a reaction mixture containing boric acid and glacial acetic acid to form a reaction product containing the sulfone.

In an embodiment of this invention, hydrogen peroxide is a preferred oxidizing agent. In accordance with this embodiment, the 2-(methylthio)-5-(trifluoromethyl)-1,3,4-thiadiazole is reacted with hydrogen peroxide in the presence of boric acid and glacial acetic acid. The hydrogen peroxide used in the reaction mixture is preferably an aqueous solution containing from about 30 weight percent to about 50 weight percent hydrogen peroxide. The hydrogen peroxide is present in a molar excess relative to the 2-(methylthio)-5-(trifluoromethyl)-1,3,4-thiadiazole. Preferably, the molar ratio of hydrogen peroxide to 2-(methylthio)-5-(trifluoromethyl)-1,3,4-thiadiazole is from about 2.0:1 to about 3.0:1. Even more preferably, the molar ratio is from about 2.05:1 to about 2.5:1. The boric acid is present in an amount of from about 0.1 moles to about 0.5 moles of boric acid per mole of 2-(methylthio)-5-(trifluoromethyl)-1,3,4-thiadiazole. Preferably, the molar ratio of boric acid to 2-(methylthio)-5-(trifluoromethyl)-1,3,4-thiadiazole is from about 0.2:1 to about 0.3:1. The glacial acetic acid is present in an amount of from about 0.1 moles to about 0.5 moles of acetic acid per mole of 2-(methylthio)-5-(trifluoromethyl)-1,3,4-thiadiazole. In a preferred embodiment, the molar ratio of glacial acetic acid to 2-(methylthio)-5-(trifluoromethyl)-1,3,4-thiadiazole is from about 0.2:1 to about 0.3:1. Oxidation typically occurs at a temperature of from about 60° C. to about 110° C. and, preferably at a temperature of from about 70° C. to about 100° C.

The process of the present invention can include additional steps. Sulfuric acid can be added to the reaction mixture to acidify the mixture. Further, water can be removed from the reaction product. The removal of water is preferably accomplished azeotropically.

Still further, an embodiment of this invention can include the step of isolating the 2-(methylsulfonyl)-5-(trifluoromethyl)-1,3,4-thiadiazole product. Following completion of the reaction, an aqueous phase and an organic phase are formed. The aqueous phase contains no solids, only a solution of boric acid and acetic acid in water. The 2-(methylsulfonyl)-5-(trifluoromethyl)-1,3,4-thiadiazole is contained in the organic phase of the reaction mixture.

A process for making 2-(methylsulfonyl)-5-(trifluoromethyl)-1,3,4-thiadiazole by oxidizing 2-(methylthio)-5-(trifluoromethyl)-1,3,4-thiadiazole in a reaction mixture containing an activated molybdenum or tungsten catalyst, is disclosed in Patent application Ser. No. 08/989,568. The activated molybdenum or tungsten catalyst in the invention is molybdic acid or tungstic acid, respectively. The reaction of the process is carried out in the absence of glacial acetic acid.

A process for making 2-(methyl-sulfonyl)-5-(trifluoromethyl)-1,3,4-thiadiazole by oxidizing 2-(methylthio)-5-(trifluoromethyl)-1,3,4-thiadiazole in the presence of a glacial acetic acid catalyst is disclosed in Patent application Ser. No. 08/989,594.

A process for making 2-(methylsulfonyl)-5-(trifluoromethyl)-1,3,4-thiadiazole comprising oxidizing 2-(methylthio)-5-(trifluoromethyl)-1,3,4-thiadiazole in a reaction mixture containing glacial acetic acid and a catalytic amount of a tungsten catalyst to form a reaction product that contains the TDA sulfone, is disclosed in Patent Application No. (MD-98-10).

DETAILED DESCRIPTION OF THE INVENTION

The present invention provides a process for producing thiadiazole sulfones. The present process is used to make 2-(methyl-sulfonyl)-5-(trifluoromethyl)-1,3,4-thiadiazole (TDA sulfone) from 2-(methylthio)-5-(trifluoromethyl)-1,3,4-thiadiazole (TDA). TDA sulfone is made using catalytic oxidation of TDA in the presence of a suitable oxidizing agent. The catalyst used for the oxidation reaction is a combination of boric acid and glacial acetic acid.

The process of the invention includes the step of oxidizing 2-(methylthio)-5-(trifluoromethyl)-1,3,4-thiadiazole (TDA) in a reaction mixture containing boric acid and glacial acetic acid, to form a reaction product that contains the TDA sulfone. Oxidation of TDA takes place in the presence of a suitable oxidizing agent. Exemplary such oxidation agents are well known in the art (See, e.g., Durst, T., in *Comprehensive Organic Chemistry:* Chapter 11.6, Barton and Ollis, Eds., Pergammon Press, Oxford, (1979). A preferred oxidizing agent is hydrogen peroxide ($H_2O_2$). In accordance with this embodiment, TDA is reacted with hydrogen peroxide in the presence of boric acid and glacial acetic acid. The hydrogen peroxide used in the reaction mixture is preferably an aqueous solution containing from about 30 weight percent to about 50 weight percent hydrogen peroxide. The molar ratio of $H_2O_2$ to TDA is from about 2.0:1 to about 3.0:1 and, preferably, from about 2.05:1 to about 2.5:1. Oxidation conditions are well known in the art. Typically, oxidation is carried out at a temperature of from about 60° C. to about 110° C., and preferably at a temperature of from about 70° C. to about 100° C.

The TDA used in the present process can be obtained from any source. Preferably, the TDA is prepared by a process that provides TDA in an aprotic, aromatic solvent such as toluene. Especially preferred means for making TDA can be found in the U.S. Patent applications entitled "A Process for Making 2-(Methylthio)-5-(Trifluoromethyl)-1,3,4-Thiadiazole Using Methyldithiocarbazinate and Trifluoroacetic Acid" (Ser. No. 08/989,152, filed Dec. 12, 1997), "A Process for Making 2-(Methylthio)-5-(Trifluoromethyl)-1,3,4-Thiadiazole Using Methyldithiocarbazinate with Trifluoroacetic Acid with Selective Removal of 2,5-Bis (Methylthio)-1,3,4-Thiadiazole" (Ser. No. 08/989,563, filed Dec. 12, 1997), and "A Process for Preparing 2-(Methylthio)-5-(Trifluoromethyl)-1,3,4-Thiadiazole Using Methyldithiocarbazinate and a Molar Excess of Trifluoroacetic Acid With Recovery of Trifluoroacetic Acid," (Ser. No. 08/989,485, filed Dec. 12, 1998). The disclosures of all three applications are incorporated herein by reference.

The oxidation of TDA occurs in the presence of a solvent. Preferably, the solvent is an aprotic, aromatic solvent. Such solvents are well known in the art. Exemplary and preferred such solvents are toluene, xylene, cumene and mesitylene. Toluene is especially preferred. The amount of solvent used can vary over a wide range as readily determined by a skilled artisan. The precise amount of solvent will depend on the particular solvent used. Where toluene is the solvent, it is present in an amount of from about 0.5 mole to about 3.5 moles of toluene per mole of TDA. Preferably, toluene is present in an amount of from about 1.0 mole to about 2.0 moles per mole of TDA and, more preferably in an amount of from about 1.0 mole to about 1.5 moles of toluene per mole of TDA.

TDA is oxidized in a reaction mixture containing boric acid and glacial acetic acid, to form a reaction product that contains TDA sulfone. Sources of TDA, use of a solvent, oxidation conditions and choice of suitable oxidizing agents are the same as set forth above. The oxidizing agent (e.g., hydrogen peroxide) used in the reaction mixture is preferably present in a molar excess relative to the TDA. Preferably, the molar ratio of oxidizing agent to TDA is from about 2.0:1 to about 3.0:1. Even more preferably, that ratio is from about 2.05:1 to about 2.5:1. The boric acid and glacial acetic acid are added directly to the reaction mixture. Boric acid is present in an amount of from about 0.1 mole to about 0.5 mole of boric acid per more of TDA. Preferably, the molar ratio of boric acid to TDA is from about 0.2:1 to about 0.3:1. Glacial acetic acid is present in an amount of from about 0.1 mole to about 0.5 mole of acetic acid per mole of TDA. In a preferred embodiment, the molar ratio of glacial acetic acid to TDA is from about 0.2:1 to about 0.3:1.

In an embodiment of the present invention, sulfuric acid in an amount less than or equal to about 0.5 mole can be added to the reaction mixture to acidify the mixture. Further, water can be removed from the reaction product. Still further, a process of this invention can include the step of isolating the formed sulfone.

Water removal is preferably accomplished azeotropically. The azeotropic removal of water is readily accomplished in the presence of the solvent, particularly where the solvent is toluene. Because the azeotrope has a lower boiling point than water, heating the reaction product to the boiling point of the solvent effectively removes the water. Because the oxidation reaction occurs in the range of about 60° C. to about 110° C., water is removed during that reaction; no additional step is required.

The following Example illustrates a preferred embodiment of the present invention and is not limiting of the specification and claims.

EXAMPLE

Synthesis of TDA Sulfone Using Boric Acid and Glacial Acetic Acid

About 1.5 moles of TDA in toluene, about 30 grams (0.49 mole) of boric acid, and about 40 grams (0.67 mole) of glacial acetic acid were charged to a reactor vessel. The reaction mixture was then heated to a temperature of about 80° C., and 3.65 moles of 35% hydrogen peroxide was added over a time period of about 4 hours. The resulting mixture was then heated for a period of about 4 hours, and water was azeotropically removed. The average percent yield and percent purity of the TDA sulfone was about 95.0% and 99.2%, respectively.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for making 2-(methylsulfonyl)-5-(trifluoromethyl)-1,3,4-thiadiazole comprising oxidizing 2-(methylthio)-5-(trifluoromethyl)-1,3,4-thiadiazole in a reaction mixture containing an oxidizing agent, boric acid, and glacial acetic acid, to form a reaction product, wherein the molar ratio of glacial acetic acid to 2-(methylthio)5-(trifluoromethyl)-1,3,4-thiadiazole is from about 0.1:1 to about 0.5:1.

2. The process of claim 1 wherein the molar ratio of boric acid to 2-(methylthio)-5-(trifluoromethyl)-1,3,4-thiadiazole is from about 0.1:1 to about 0.5:1.

3. The process of claim 1 wherein the oxidizing agent is hydrogen peroxide.

4. The process of claim 1 wherein the 2-(methylthio)-5-(trifluoromethyl)-1,3,4-thiadiazole is dissolved in an aprotic, aromatic solvent.

5. The process of claim 4 wherein the solvent is toluene.

6. The process of claim 5 wherein the molar ratio of toluene to 2-(methylthio)-5-(trifluoromethyl)-1,3,4-thiadiazole is from about 0.5:1 to about 3.5:1.

7. The process of claim 6 wherein the molar ratio of toluene to 2-(methylthio)-5-(trifluoromethyl)-i ,3,4-thiadiazole is from about 1:1 to about 1.5:1.

8. The process of claim 1 wherein oxidation occurs at a temperature of from about 60° C. to about 110° C.

9. The process of claim 8 wherein the temperature is from about 70° C. to about 100° C.

10. The process of claim 3 wherein the molar ratio of hydrogen peroxide to 2-(methylthio)-5-(trifluoromethyl)-1,3,4-thiadiazole is from about 2.0:1 to about 3.0:1.

11. The process of the claim 10 wherein the molar ratio of hydrogen peroxide to 2-(methylthio)-5-(trifluoromethyl)-1,3,4 thiadiazole is from about 2.05:1 to about 2.50:1.

12. The process of claim 1 wherein the molar ratio of glacial acetic acid to 2-(methylthio)-5-(trifluoromethyl)-1,3,4-thiadiazole is from about 0.2:1 to about 0.3:1.

13. The process of claim 1 further comprising azeotropically removing water from the reaction product.

14. The process of claim 1 further comprising isolating the formed 2-(methylsulfonyl)-5-(trifluoromethyl)-1,3,4-thiadiazole.

* * * * *